United States Patent [19]

Hope

[11] Patent Number: Plant 5,387

[45] Date of Patent: Jan. 8, 1985

[54] KALANCHOE PLANT NAMED CANCUN

[75] Inventor: Claude Hope, Cartago, Costa Rica

[73] Assignee: Pan American Plant Company, Parrish, Fla.

[21] Appl. No.: 496,304

[22] Filed: May 19, 1983

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A new and distinct Kalanchoe plant named Cancun, characterized by its early flowering response, highly floriferous habit, orange flower color with yellow eye, compact habit, fast growth rate, free branching, average 11 week flowering response, and its adaptability to production in 10–15 cm. pots.

1 Drawing Figure

The present invention relates to a new and distinctive cultivar of Kalanchoe plant, botanically known as Kalanchoe, and referred to by the cultivar name Cancun.

The new cultivar was referred to during the selection process by the designation Tetravulcan-3-4-1-1-4-12, and is a product of a planned breeding program. Cancun was later recoded K78-66N when received by Pan American Plant Company in West Chicago, Ill. in 1978. The basic objection of the breeding program was to create a new Kalanchoe cultivar having orange flower color with yellow eye, early flowering response, compact habit, and the ability to produce commercially acceptable quality in a year-round Kalanchoe program.

The new cultivar was originated from a self pollination of Tetravulcan-3-4-1-1-4 made in a controlled breeding program at Linda Vista, S.A., Cartago, Costa Rica.

Cancun was discovered and selected by me as a flowering plant within the progeny of the stated self in a field of seedlings in Cartago, Costa Rica. Asexual reproduction of the new cultivar by stem cuttings, as first performed by me at Cartago, Costa Rica, and subsequently performed in West Chicago, Ill., and Parrish, Fla., has demonstrated that the combination of characteristics as herein disclosed for the new cultivar are firmly fixed and are retained through successive generations of asexual reproduction.

Cancun has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Cancun, which in combination distinguish this Kalanchoe as a new and distinct cultivar.

1. Orange flower petals with a yellow eye.
2. Compact habit and fast growth rate as compared to other cultivars.
3. Freely branching, with shoots formed at every node.
4. Suitable for production in 10 to 15 cm. pots, flowering from 10 weeks in summer to 12 weeks in winter.
5. Highly floriferous, with numerous flowers formed at every shoot.

6. To reduce peduncle elongation after flower initiation plants can be treated with B-9.

The new cultivar is most similar to Cozumel, disclosed in my pending application Ser. No. filed concurrently with the present application. Cancun is principally distinguished from Cozumel by its one week earlier flowering response, slightly darker flower color, and slightly smaller flower size. In addition, the leaves of Cancun tend to cup down at the edges (convex) where the leaves of Cozumel tend to cup upward at the edges (concave).

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under natural light conditions at approximately 3:00 P.M. under 2000 foot candies of light intensity at Parrish, Fla.

BOTANICAL CLASSIFICATION

Kalanchoe, cv. Cancun

PARENTAGE

Self-pollination of Tetravulcan-3-4-1-14.

PROPAGATION:

The new cultivar holds its distinguishing characteristics through successive propagations by leaf cuttings and by division of shoots.

Type cutting: Tip cuttings, with stems up to 2 mm. long.

Time to root: 10 Days at 21° C. summer, 14 days at 21° C. winter.

Rooting habit: Fibrous, many very fine roots.

PLANT DESCRIPTION

Form: Upright, medium height, compact. Growing and scheduling practices can produce small plants in 10 cm. pots or larger plants in 15 cm. pots.

Habit of growth: Fast growth rate for this type of plant. Shoots are normally formed at every node.

Foliage description: Leaves simple, opposite, generally symmetrical.

1. *Size.*—Average full-grown leaf of a flowering plant in a 10 cm. pot is 90–120 cm. long and 70–110 cm. wide. Plants in larger pots generally have proportionately larger leaves.

2. *Shape.*—Ovate, apex obtuse, base truncate to acute.
3. *Texture.*—Glabrous, coriaceous, succulent.
4. *Margin.*—Crenate.
5. *Color.*—Young foliage top side, 147A, under side, 147B. Mature foliage top side 147A, under side 147B.

FLOWERING DESCRIPTION

Flowering habit: Infloresence of each shoot is formed by dichotomous branching, starting with opening of terminal flower of main axis followed by terminal flowers of the side branches of the inflorescence. Opening of new buds will continue for 2 months or more. Individual flowers last 2 weeks or more after opening.

Natural flowering season: January. Flowering time under controlled day length at 30° C. in summer is 10 weeks; in winter at 20° C., 12 weeks. Flowering time depends on temperature, light intensity and other growing conditions.

Flower buds: Oblong, developing to tubular as petals mature, sheathed with four green sepals; corolla at maturity 11 mm. long.

1. *Size.*—Up to 10 mm.
2. *Shape.*—Oblong.
3. *Rate of opening.*—Normal.

Flowers borne: Compound dichasial cyme on strong peduncles, peduncle length depends on growing conditions and B-9 applications. Pedicels up to 5 mm. long.

Quantity of flowers: Very floriferous with new buds continuing to develop.

Petals:

1. *Shape.*—Nearly round, apex cuspidate.
2. *Color.*—Top side when opening, 33A, fading to 33C; under side, 29C.
3. *Number and size of petals.*—4; 5 mm. in diameter; total flower diameter 14 mm.

Reproductive organs:

1. *Stamens.*—Eight (8) in number. (a) Anther shape: flat, elliptical. (b) Filament color: Yellow. (c) Pollen color: Yellow.
2. *Pistels.*—(a) Stigma shape: flat, crystalline. (b) Style color: Greenish-white. (c) Ovaries: 4 celled, 5 mm. long, green.

DISEASE RESISTANCE

No known Kalanchoe diseases observed to date.

I claim:

1. A new and distinct Kalanchoe plant names Cancun, as described and illustrated, and particularly characterized by its early flowering response, highly floriferous habit, orange flower color with yellow eye, compact habit, fast growth rate, free branching, average 11 week flowering response, and its adaptability to production in 10–15 cm. pots.

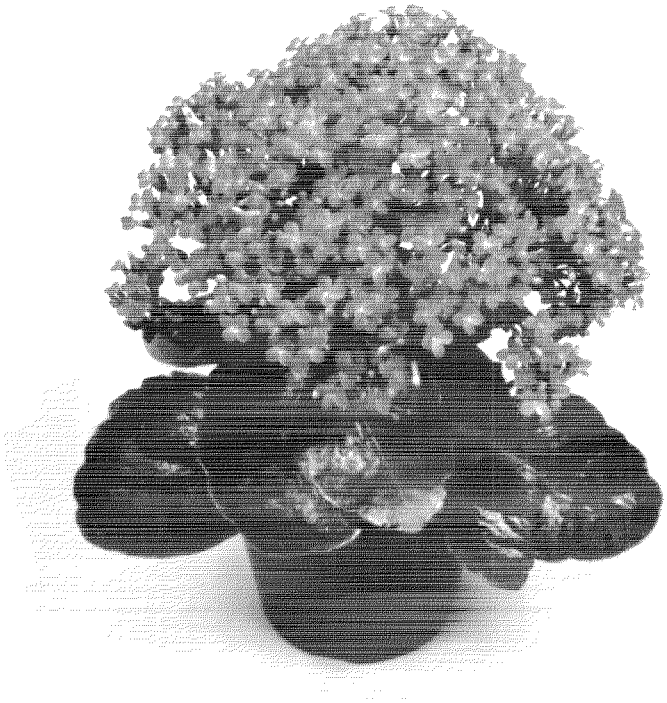

* * * * *